(12) United States Patent
Bair et al.

(10) Patent No.: US 12,303,168 B2
(45) Date of Patent: *May 20, 2025

(54) UTERINE HEMORRHAGE CONTROLLING SYSTEM AND METHOD

(71) Applicant: ALYDIA HEALTH, INC., Menlo Park, CA (US)

(72) Inventors: Nathaniel Bair, San Luis Obispo, CA (US); Amelia Degenkolb, San Luis Obispo, CA (US); Sara Ripa, San Luis Obispo, CA (US); Jan Segnitz, San Luis Obispo, CA (US)

(73) Assignee: ALYDIA HEALTH, INC., Menlo Park, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 18/052,358

(22) Filed: Nov. 3, 2022

(65) Prior Publication Data

US 2023/0093148 A1 Mar. 23, 2023

Related U.S. Application Data

(63) Continuation of application No. 15/683,561, filed on Aug. 22, 2017, now Pat. No. 11,517,336.
(Continued)

(51) Int. Cl.
*A61B 17/42* (2006.01)
*A61B 17/00* (2006.01)
(Continued)

(52) U.S. Cl.
CPC ........ *A61B 17/42* (2013.01); *A61B 17/22004* (2013.01); *A61M 1/784* (2021.05);
(Continued)

(58) Field of Classification Search
CPC .. A61M 1/84; A61M 25/007; A61M 25/0041; A61M 27/00; A61M 25/0043;
(Continued)

(56) References Cited

U.S. PATENT DOCUMENTS 2,185,927 A 1/1940 Shelanski
2,400,251 A 5/1946 Nagel
(Continued)

FOREIGN PATENT DOCUMENTS

CA 2952904 10/2015
CN 2097618 U 3/1992
(Continued)

OTHER PUBLICATIONS

Cook, "Balloon Uterine Stent", retrieved from <www.cookmedical.com/products/wh bus webds/>, Dec. 12, 2017, 3 pages.
(Continued)

*Primary Examiner* — Adam Marcetich
(74) *Attorney, Agent, or Firm* — Jordan IP Law, LLC

(57) ABSTRACT

An insertable device is designed to control uterine hemorrhaging after birth by facilitating contractile movement of the uterus. An insertable device comprises a tube having a connecting portion and a suction portion and a seal positioned along the length of the connecting portion proximal to the suction portion. Upon insertion of the suction portion and seal into the uterus, the seal abuts a vaginal canal and forms a seal between a vaginal opening and the uterus. The suction portion comprises a first loop having an opening that is oriented away from an interior wall of the uterus when inserted into the uterus. The connecting portion of the tube couples to a pump that when actuated generates a negative pressure within the uterus, resulting in a uniform mechanical stimulus to the uterine wall in order to facilitate tamponade and contractile movement of the tissue.

20 Claims, 12 Drawing Sheets

Related U.S. Application Data

(60) Provisional application No. 62/378,889, filed on Aug. 24, 2016.

(51) Int. Cl.
*A61B 17/22* (2006.01)
*A61M 1/00* (2006.01)

(52) U.S. Cl.
CPC ..... *A61M 1/84* (2021.05); *A61B 2017/00305* (2013.01); *A61B 2017/00561* (2013.01); *A61B 2017/22079* (2013.01); *A61B 2017/4216* (2013.01); *A61M 2210/1433* (2013.01)

(58) Field of Classification Search
CPC ...... A61M 2025/0034; A61M 25/0009; A61M 25/0068; A61M 25/00; A61M 25/0021; A61M 25/005; A61M 1/77; A61B 17/42; A61B 2217/005; A61B 17/12136; A61B 17/4241; A61B 1/303; A61B 2017/4216; A61B 2017/4225

See application file for complete search history.

(56) References Cited

U.S. PATENT DOCUMENTS

| | | | |
|---|---|---|---|
| 2,981,255 A | 4/1961 | Heyns | |
| 3,062,215 A | 11/1962 | Heyns | |
| 3,517,655 A | 6/1970 | Sheldon | |
| 3,626,928 A | 12/1971 | Barringer et al. | |
| 3,670,732 A | 6/1972 | Robinson | |
| 3,774,613 A | 11/1973 | Woods, Jr. et al. | |
| 3,777,743 A * | 12/1973 | Binard | A61B 10/0291 606/119 |
| 3,828,781 A | 8/1974 | Rothman | |
| 3,835,843 A | 9/1974 | Karman | |
| 3,848,602 A | 11/1974 | Gutnick | |
| 3,923,051 A | 12/1975 | Soichet | |
| 3,929,133 A | 12/1975 | Ragab | |
| 4,013,079 A | 3/1977 | Lindemann et al. | |
| 4,100,923 A * | 7/1978 | Southern | A61D 19/04 604/920 |
| 4,111,209 A | 9/1978 | Wolvek et al. | |
| 4,141,360 A | 2/1979 | Lasswell | |
| 4,444,548 A | 4/1984 | Andersen et al. | |
| 4,533,345 A | 6/1985 | Louw | |
| 4,552,557 A | 11/1985 | Rangaswamy | |
| 4,563,183 A | 1/1986 | Barrodale et al. | |
| 4,681,123 A | 7/1987 | Valtchev | |
| 4,784,654 A | 11/1988 | Beecher | |
| 4,807,625 A | 2/1989 | Singleton | |
| 4,925,452 A | 5/1990 | Melinyshyn et al. | |
| 4,955,875 A | 9/1990 | Knowles | |
| 4,981,477 A | 1/1991 | Schon et al. | |
| 5,030,202 A | 7/1991 | Harris | |
| 5,100,395 A | 3/1992 | Rosenberg | |
| 5,104,377 A | 4/1992 | Levine | |
| 5,209,754 A * | 5/1993 | Ahluwalia | A61B 17/4241 606/1 |
| 5,242,438 A | 9/1993 | Saadatmanesh et al. | |
| 5,360,414 A | 11/1994 | Yarger | |
| 5,372,584 A * | 12/1994 | Zink | A61B 10/0291 604/97.02 |
| 5,431,173 A | 7/1995 | Chin et al. | |
| 5,451,208 A | 9/1995 | Goldrath | |
| 5,464,409 A | 11/1995 | Mohajer | |
| 5,472,435 A | 11/1995 | Sutton | |
| 5,569,284 A | 10/1996 | Young et al. | |
| 5,603,685 A | 2/1997 | Tulrome, Jr. | |
| 5,769,880 A | 6/1998 | Truckai et al. | |
| 5,807,282 A | 9/1998 | Fowler | |
| 5,836,913 A * | 11/1998 | Orth | A61B 17/3417 604/174 |
| 5,935,098 A * | 8/1999 | Blaisdell | A61M 25/04 604/515 |
| 6,350,463 B1 | 2/2002 | Herman et al. | |
| 6,443,947 B1 | 9/2002 | Marko et al. | |
| 6,506,149 B2 | 1/2003 | Peng et al. | |
| 6,508,815 B1 | 1/2003 | Strul et al. | |
| 6,626,826 B1 * | 9/2003 | Van Der Weegen | A61B 1/00082 600/119 |
| 6,641,575 B1 | 11/2003 | Lonky | |
| 6,676,680 B1 | 1/2004 | Packer | |
| 6,736,822 B2 | 5/2004 | McClellan et al. | |
| 7,247,141 B2 | 7/2007 | Makin et al. | |
| 7,325,546 B2 | 2/2008 | Burbank et al. | |
| 7,512,445 B2 | 3/2009 | Truckai et al. | |
| 7,708,716 B2 | 5/2010 | Shah | |
| 8,197,470 B2 | 6/2012 | Sharkey et al. | |
| 8,221,401 B2 | 7/2012 | Sharkey et al. | |
| 8,287,552 B2 | 10/2012 | Grillo | |
| 9,125,686 B2 | 9/2015 | Norred et al. | |
| 9,301,770 B2 | 4/2016 | Gruber | |
| 9,550,014 B2 | 1/2017 | Norred et al. | |
| 9,763,731 B2 | 9/2017 | Dubois et al. | |
| 9,919,083 B2 | 3/2018 | Blin | |
| 10,064,651 B2 | 9/2018 | Norred et al. | |
| 2003/0064746 A1 | 4/2003 | Rader et al. | |
| 2003/0191452 A1 | 10/2003 | Meglin et al. | |
| 2005/0261663 A1 | 11/2005 | Patterson et al. | |
| 2006/0015089 A1 | 1/2006 | Meglin et al. | |
| 2007/0032814 A1 | 2/2007 | Hibler | |
| 2007/0149998 A1 | 6/2007 | Wicks et al. | |
| 2008/0045924 A1 | 2/2008 | Cox et al. | |
| 2008/0051708 A1 | 2/2008 | Kumar et al. | |
| 2009/0048685 A1 | 2/2009 | Frigstad et al. | |
| 2009/0093795 A1 | 4/2009 | Koeper | |
| 2010/0069886 A1 | 3/2010 | Wilkes | |
| 2010/0180422 A1 * | 7/2010 | Valtchev | A61B 17/4241 606/119 |
| 2010/0198214 A1 | 8/2010 | Layton, Jr. et al. | |
| 2010/0228239 A1 | 9/2010 | Freed | |
| 2011/0087337 A1 | 4/2011 | Forsell | |
| 2011/0098524 A1 | 4/2011 | Barcelo Rojas | |
| 2011/0208178 A1 | 8/2011 | Truckai | |
| 2012/0053503 A1 | 3/2012 | Patterson et al. | |
| 2013/0245637 A1 | 9/2013 | Norred et al. | |
| 2013/0266165 A1 | 10/2013 | Neumeyer | |
| 2014/0079241 A1 | 3/2014 | Chan et al. | |
| 2014/0163532 A1 | 6/2014 | Cornet et al. | |
| 2014/0200591 A1 | 7/2014 | Sullivan et al. | |
| 2014/0228801 A1 | 8/2014 | Kelling | |
| 2015/0127016 A1 * | 5/2015 | Sauer | A61B 17/4241 606/119 |
| 2015/0133923 A1 * | 5/2015 | Batchelor | A61B 18/1485 606/48 |
| 2015/0165151 A1 | 6/2015 | Payton et al. | |
| 2016/0166805 A1 * | 6/2016 | Hahne | A61M 25/0017 604/28 |
| 2016/0270819 A1 * | 9/2016 | Ahluwalia | A61B 17/4241 |
| 2017/0035949 A1 | 2/2017 | Loske | |
| 2017/0281231 A1 | 10/2017 | Langell et al. | |
| 2017/0354436 A1 * | 12/2017 | Holbrooks | A61B 17/42 |
| 2019/0216504 A1 | 7/2019 | Norred et al. | |

FOREIGN PATENT DOCUMENTS

| | | |
|---|---|---|
| CN | 2116469 U | 9/1992 |
| CN | 2149183 Y | 12/1993 |
| CN | 2254720 Y | 5/1997 |
| CN | 2415733 Y | 1/2001 |
| CN | 2464264 Y | 12/2001 |
| CN | 2467062 Y | 12/2001 |
| CN | 2559321 Y | 7/2003 |
| CN | 2565407 | 8/2003 |
| CN | 2633227 Y | 8/2004 |
| CN | 2662850 | 12/2004 |
| CN | 201185945 Y | 1/2009 |
| CN | 101366650 A | 2/2009 |
| CN | 201337472 Y | 11/2009 |
| CN | 201356633 | 12/2009 |
| CN | 201361088 Y | 12/2009 |

(56) References Cited

FOREIGN PATENT DOCUMENTS

| | | |
|---|---|---|
| CN | 202044560 U | 11/2011 |
| CN | 202146327 U | 2/2012 |
| CN | 202288422 U | 7/2012 |
| CN | 203122506 U | 8/2013 |
| CN | 106390212 A | 2/2017 |
| CN | 106821472 A | 6/2017 |
| CN | 206587003 U | 10/2017 |
| CN | 206852626 U | 1/2018 |
| CN | 207220865 U | 4/2018 |
| DE | 102014005679 A1 | 10/2015 |
| GB | 839965 A | 6/1960 |
| GB | 1469584 A | 4/1977 |
| IN | 20030006513 | 1/2005 |
| IN | 4745CHE2015 | 8/2016 |
| JP | 2001513357 A | 9/2001 |
| JP | 2007523716 A | 8/2007 |
| JP | 2015512275 A | 4/2015 |
| KR | 20010002164 A | 1/2001 |
| RU | 2113246 C1 | 6/1998 |
| RU | 98112 | 10/2010 |
| RU | 102509 U1 | 3/2011 |
| RU | 2429792 C1 | 9/2011 |
| RU | 2440038 C2 | 1/2012 |
| SU | 1431746 A1 | 10/1988 |
| WO | 2001080788 A2 | 11/2001 |
| WO | 2012137894 A1 | 10/2012 |
| WO | 2013138625 A1 | 9/2013 |

OTHER PUBLICATIONS

Cook, "Manage Postpartum Hemorrhage, Bakri, Postpartum Balloon With Rapid Instillation Components," retrieved from <www.cookmedical.com/data/recorces/RHD28438-EN-F>, Dec. 21, 2017, 4 pages.

Video of Panickers PPH Suction Device, Vasudeva Panicker, Apr. 9, 2015, May be Viewed at <URL:https://www.youtube.com/watch?v=KDa tlp3qVM>.

Video of Dr. Panicker's PPH Suction Device—Instastop, Vasudeva Panicker, Jan. 26, 2017, May be Viewed at <URL:https://www.youtube.com/watch?v=a-QlpkeT3Gg>.

Video of PPH Suction, Vasudeva Panicker, Oct. 25, 2016, May be Viewed at <URL:https://www.voutube.com/watch?v=uQYoWEbWJOg>.

Panicker, T.N.V., "Panicker's Vacuum Suction Haemostatic Device for Treating Post-Partum Haemorrhage," The Journal of Obstetrics and Gynecology of India, Mar.-Apr. 2017, pp. 150-151, vol. 67, No. 2, May be Retrieved at <URL:http://www.jogi.co.in/march april 17 /pdf/14 iat.pdf>.

Purwosunu et al.; "Control of postpartum hemorrhage using vacuum-induced uterine tamponade", Obstetrics and Gynecology, Jul. 2016, pp. 33-36.

Hofmeyr, J.; Uterine suction devices: Review of literature and potential role; Effective care research unit, Univ. of the Witwatersrand/ Fort Hare/Eastern Cape Dept. of Health; 22 pages; known of at least by Nov. 2018.

Examination Report for Australian Application No. 2017316656, mailed May 5, 2022, 6 pages.

Examination Report for Brazilian Application No. 112019003632-6, mailed Mar. 21, 2023, 5 pages.

Decision to Grant for Japanese Application No. 2019-531864, mailed Feb. 7, 2023, 5 pages.

Examination Report for European Application No. 17844298.4, mailed Apr. 17, 2023, 5 pages.

* cited by examiner

UTERINE HEMORRHAGE CONTROLLING SYSTEM AND METHOD

CROSS REFERENCE TO RELATED APPLICATIONS

This application is a divisional of U.S. patent application Ser. No. 15/683,561, filed Aug. 22, 2017, which claims the benefit of U.S. Provisional Application No. 62/378,889, filed Aug. 24, 2016, which are each incorporated by reference in their respective entireties.

BACKGROUND

Postpartum hemorrhage, defined as excessive blood loss after birth, is the leading cause of maternal death in the world, claiming the lives of over 125,000 mothers every year. Inability to control postpartum bleeding can require a woman to receive multiple blood transfusions, and in severe cases, a full hysterectomy or death. Therefore, it is desirable to control such postpartum bleeding, if possible, at its onset. The cause of postpartum hemorrhage, in approximately 80% of cases, is uterine atony, which is the inability of the woman's uterus to contract after delivering the child. Risk factors for uterine atony include prolonged stage of labor, preeclampsia, and multiparity. Accordingly, a system that is able to rapidly induce uterine contraction, which may reduce or entirely stop uterine hemorrhaging, is needed.

SUMMARY

An insertable device is insertable into a uterus. The insertable device comprises a connecting portion and a suction portion of a tube and a seal. The connecting portion of the tube couples to a pump that, when actuated, generates a change in pressure. The suction portion of the tube inserts into a uterus, and the suction portion comprises a first loop comprising an opening defined along a medial surface of the first loop. The opening is oriented away from an interior wall of the uterus upon insertion of the suction portion into the uterus. The seal is positioned along a length of the connecting portion proximal to the suction portion. The seal abuts a vaginal canal upon insertion of the insertable device and forms a seal between the vaginal canal and the uterus.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Figure 1A:
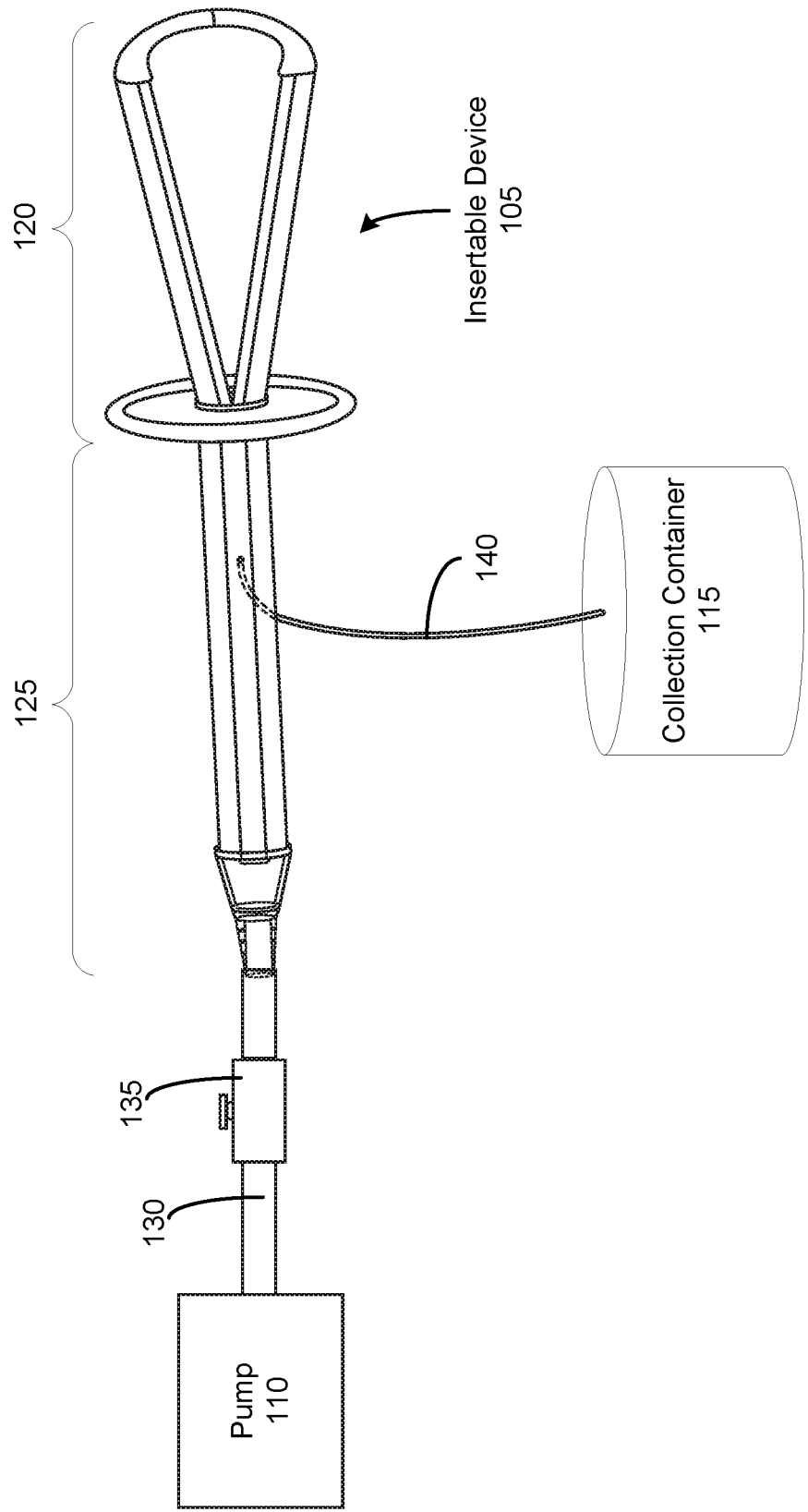
FIGS. 1A, 1B, and 1C illustrate a system for controlling uterine hemorrhaging, according to an embodiment.

FIG. 1A illustrates a system 100 for controlling uterine hemorrhaging, according to an embodiment. The system 100 functions to reduce or entirely stop uterine hemorrhaging, which may occur after childbirth when a woman experiences uterine atony, wherein the uterus fails to contract. Controlling uterine hemorrhaging substantially reduces the total blood lost from the uterus and may reduce a woman's need for a blood transfusion or a hysterectomy. In the embodiment of FIG. 1A, the system 100 facilitates contraction of the uterus by sealing an opening to the uterus and providing a pressure change within the uterus. Changing the pressure generates a vacuum within the uterus that results in a uniform mechanical stimulus to the uterine wall in order to facilitate tamponade and contractile movement of the tissue. In the embodiment of FIG. 1A, the system 100 includes an insertable device 105, a pump 110, and a collection container 115.

The insertable device 105 is configured to be inserted into the uterus to transmit the pressure change provided by the pump 110. In the embodiment of FIG. 1A, the insertable device 105 is delivered transvaginally (through the vagina) such that a distal portion 120 of the insertable device 105 is positioned within the uterus while a proximal portion 125 of the insertable device 105 remains external to the uterus. The distal portion 120 may have a flexible structure such that it conforms to the anatomy of the uterus and allows the distal portion 120 to create a seal at the opening of the uterus. The proximal portion 125 of the insertable device 105 couples to the pump 110. The distal and proximal portions 120, 125 may have one or more channels and/or openings that allow fluid communication (e.g., of air, biological materials, etc.) between the uterus, the pump 110, and the collection container 115. The one or more channels and/or openings transfer the vacuum between the uterus and the pump 110. In some embodiments, the insertable device 105 may have a sheath that facilitates insertion of the insertable device 105 into the uterus and may additionally prevent a premature connection of the airflow from the pump 110 to the uterus. The insertable device 105 will be discussed in further detail with regards to FIG. 2.

The pump 110 creates a pressure change that generates a vacuum within the uterus. In the embodiment of FIG. 1A, the pump 110 is coupled to the proximal portion 125 of the insertable device 105. In some embodiments, a connection tubing 130 attaches to the proximal portion 125 at a first end and attaches to the pump 110 at a second end, thereby coupling the pump 110 and the insertable device 105. In some embodiments, the connection tubing 130 includes a directional control valve 135 that allows fluid to flow in one direction and prevents fluid from flowing in the opposite direction.

When actuated, the pump 110 creates an airflow that is transmitted through the channels and/or openings of the insertable device 105 to the uterus. In general, vacuum pumps are configured to remove molecules from a sealed volume in order to leave behind a partial vacuum. Since the uterus is sealed by the distal portion 120 of the insertable device 105, the airflow by the pump 110 decreases the pressure inside the uterus, causing the uterine pressure to drop lower than the atmospheric pressure outside of the uterus and resulting in a negative pressure. The negative pressure ensures that the airflow travels in a single direction from the uterus and through the insertable device 105 towards the pump 110. The negative pressure generates a vacuum inside the uterus, which facilitates tamponade, arterial vessel constriction, and contractile movement of the uterine wall by providing a uniform mechanical stimulus. In addition, generating a vacuum allows biological materials within the uterus to be removed. Biological materials may include blood, tissue, etc. The pump 110 may be power/automatically operated or manually operated. The embodiments in which the pump 110 is manually operated, the pump 110 may create a negative pressure within the uterus when in a first state, and in a second state, the pump 110 may draw biological materials into the collection container 115 while maintain the negative pressure within the uterus. While a "negative pressure" is referred to throughout, some embodiments may generate a positive pressure inside the uterus to facilitate contractions of the uterus.

The collection container 115 collects the biological materials removed from the uterus. In the embodiment of FIG. 1A, the collection container 115 is coupled to the proximal portion 125 of the insertable device 105. The collection container 115 may be coupled via a connection tubing 140 that is integrated into the proximal portion 125. When the pump 110 is actuated, the biological materials travel from the uterus, into the openings and/or channels of the insertable device 105, and through the connecting tubing 140 into the collection container 115. Collecting biological materials from the uterus may allow a user to monitor and measure the amount of blood loss due to uterine hemorrhaging. Monitoring the blood loss additionally allows the user to determine whether, when, and/or to what extent uterine contraction has occurred. In some embodiments, the collection container 115 may be configured as an inline filter that is positioned before the connection tubing 130 to the pump 110, allowing biological materials from the uterus to flow through the insertable device 105 and be filtered out before the pump 110.

In some embodiments, the system 100 may be used to prevent postpartum hemorrhage in addition to monitoring and/or treating it. For example, the system 100 may be used in any woman after birth to aid uterine contraction. The flexibility of the insertable device 105 allows a healthcare provider (e.g., nurse, physician, surgeon, etc.) to palpate a woman's uterine tissue abdominally in order to detect if and/or when the uterus has contracted. In addition, the flexibility of the insertable device 105 allows the insertable device 105 to be flexed and positioned while other vaginal wall or tissue repair surgical procedures are being conducted.

In some embodiments, the insertable device 105 may be configured for insertion into a vaginal canal or a cervical canal such that the insertable device 105 remains external to the uterus. In a similar manner as described above, the distal portion 120 creates a seal between a vaginal opening or a cervical opening and the uterus. Creating the seal allows the airflow by the pump 110 to decrease the pressure inside the uterus, causing the uterine pressure to drop lower than the atmospheric pressure outside of the uterus and generating a vacuum inside the uterus. As previously described, this facilitates tamponade, arterial vessel constriction, and contractile movement of the uterine wall by providing a uniform mechanical stimulus. This configuration of the insertable device 105 may provide a less invasive method for controlling uterine hemorrhaging.

Figure 1B:
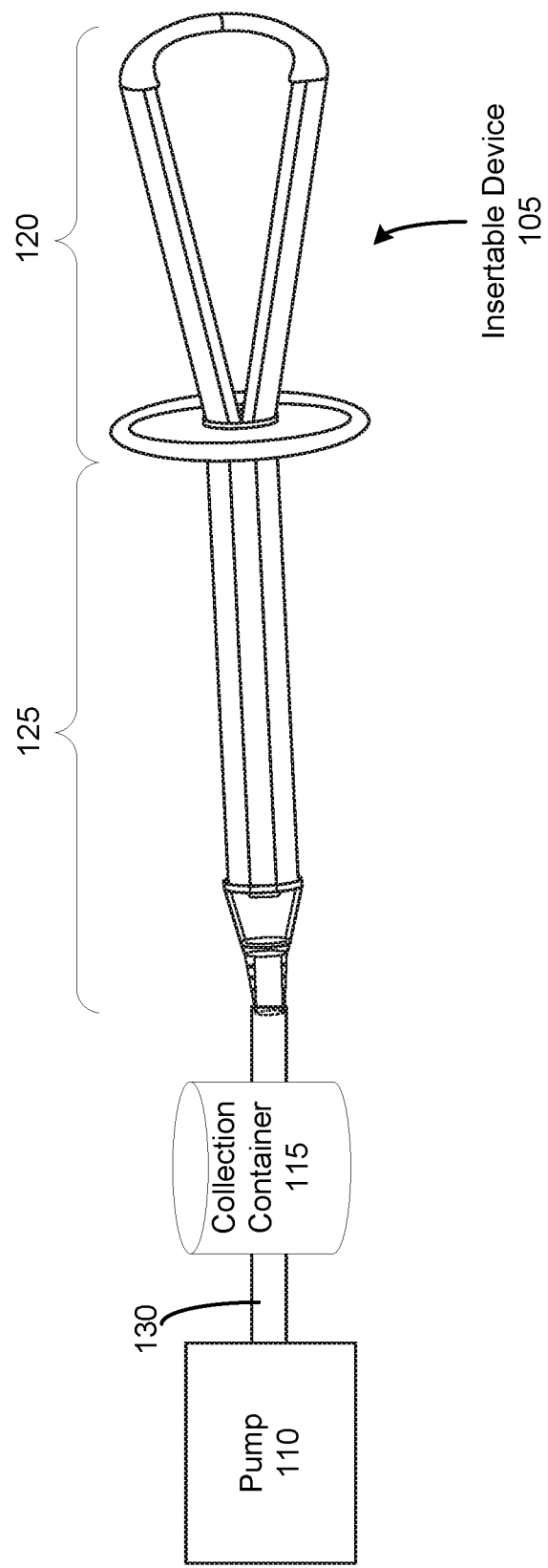

FIG. 1B illustrates a system 100 for controlling uterine hemorrhaging, according to an additional embodiment. In the embodiment of FIG. 1B, the system 100 includes an insertable device 105, a pump 110, and a collection container 115. As illustrated in FIG. 1B, the collection container 115 is connected in-line with the pump 110. The proximal portion 125 of the insertable device 105 couples to the collection container 115 and the pump 110 via the connection tubing 130. In this embodiment, the fluid (e.g., air, biological materials, etc.) flows through the connection tubing 130 towards the pump 110 when the pump 110 is activated. The biological material is removed from the connection tubing 130 prior to reaching the pump 110 and collects in the collection container 115.

Figure 1C:
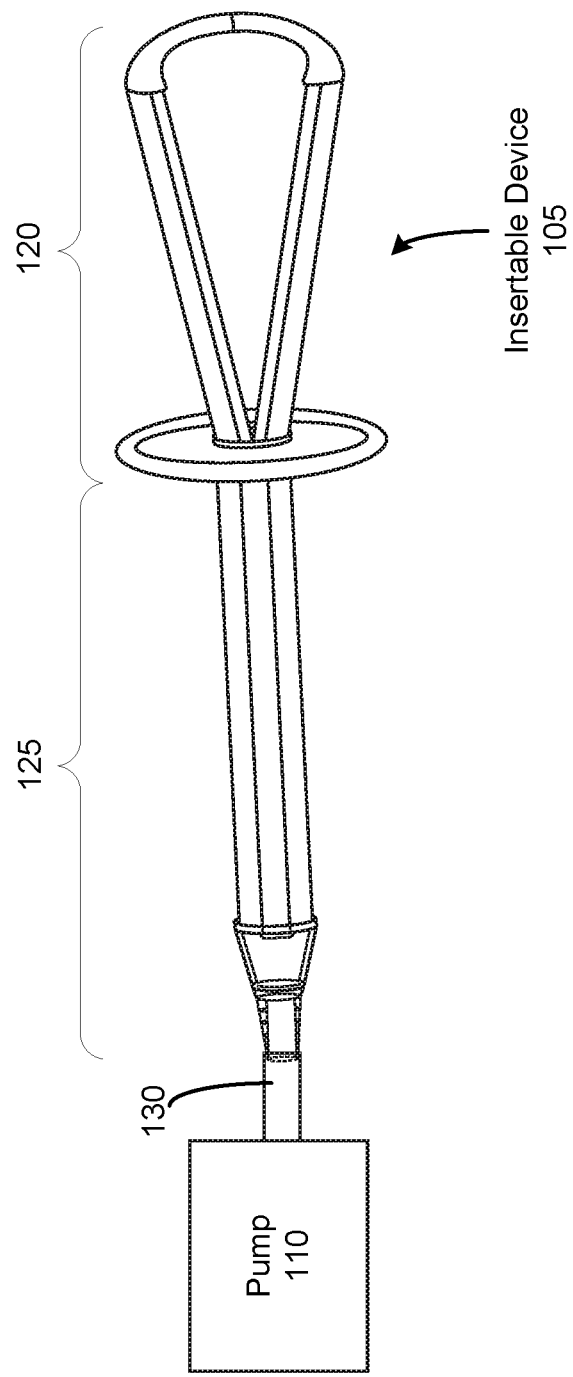

FIG. 1C illustrates a system 100 for controlling uterine hemorrhaging, according to an additional embodiment. In the embodiment of FIG. 1C, the system 100 includes an insertable device 105 and a pump 110. The proximal portion 125 of the insertable device 105 couples to the pump 110 via the connection tubing 130. In this embodiment, the collection container 115 is integrated with the pump 110 such that the fluid (e.g., air, biological materials, etc.) flows through the connection tubing 130 into the pump 110, in which the biological materials are collected into a separate compartment of the pump 110. The compartment that collects the biological material may be removable from the pump 110. This may assist a healthcare provider in monitoring the amount of biological material collected.

Figure 2:
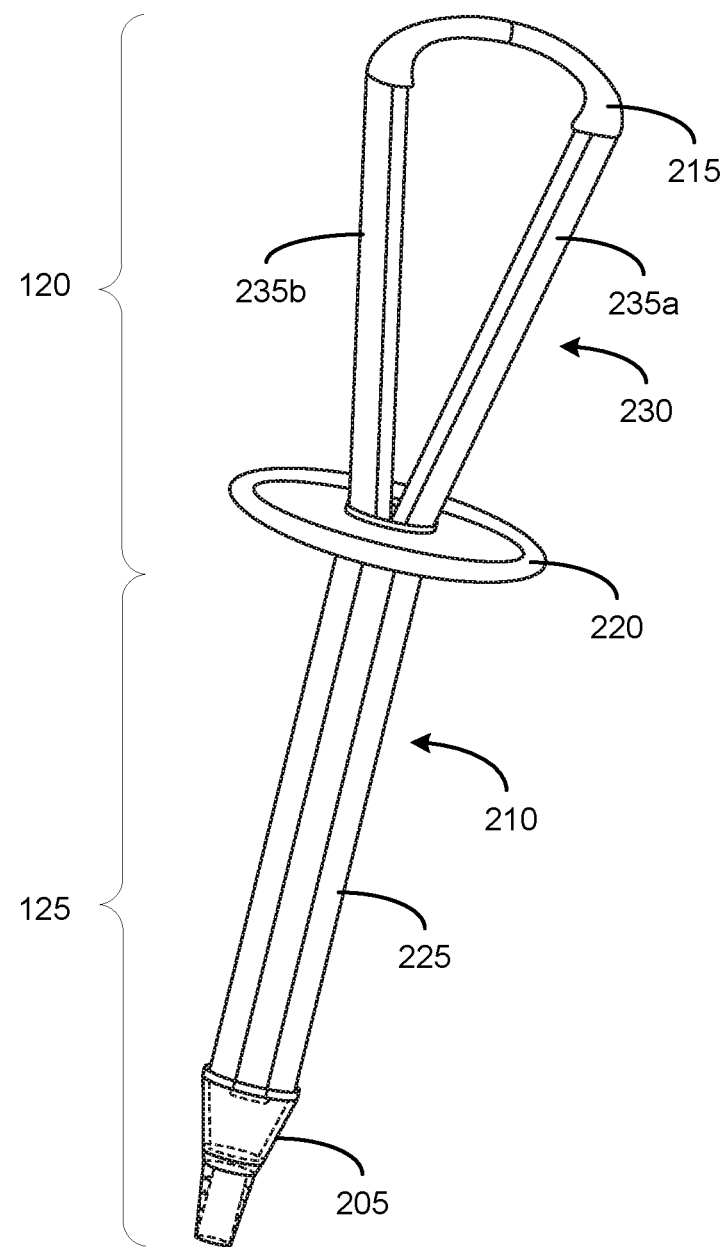
FIG. 2 illustrates an insertable device, according to an embodiment.

FIG. 2 illustrates the insertable device 105, according to an embodiment. As described with regards to FIG. 1A, the insertable device 105 is configured to be inserted into the uterus to transmit the pressure change provided by the pump 110. The distal portion 120 is inserted into the uterus and seal an opening to the uterus, and the proximal portion couples to the pump 110. In the embodiment of FIG. 2, the insertable device 105 includes a tube connector 205, a tube 210, a bridge 215, and a seal 220. The tube 210 includes a connecting portion 225 and a suction portion 230. Each component of the insertable device 105 may have a variety of designs and may be interchangeable to create alternate configurations of the insertable device 105.

The tube connector 205 couples the insertable device 105 to the pump 110. In some embodiments, the tube connector 205 couples to the pump 110 via connection tubing (e.g., connecting tubing 130). In the embodiment of FIG. 2, the tube connector 205 is tapered such that it may be inserted into the connection tubing and secured to the connection tubing via an interference it (e.g., press fit or friction fit). In the embodiment of FIG. 2, the tube connector 205 attaches to a proximal end of the connecting portion 225 of the tube 210. The tube connector 205 may be attached to the connecting portion 225 via an interference fit (e.g., press fit or friction fit), an adhesive, a threaded interface, or any other suitable securing mechanism. The tube connector 205 may be composed of rigid or semi-rigid plastic (e.g., polyethylene, polypropylene) or any other suitable material.

The tube 210 acts as a conduit for air and biological materials. The tube 210 may comprise one or more channels that couple airflow from the pump 110 to the uterus to transmit a change in pressure inside the uterus. In the embodiment of FIG. 2, the tube 210 includes a single channel having surface features on an internal surface of the channel. Alternate embodiments of the tube 210 will be discussed in further detail with regards to FIGS. 7B-7E. The internal surface features protrude from the internal surface of the channel and may aid the flow of air and biological materials through the tube 210. The internal surface features may have a variety of configurations, which will be discussed in further detail with regards to FIGS. 4-5. In the embodiment of FIG. 2, the tube 210 includes the connecting portion 225 and the suction portion 230.

The connecting portion 225 transmits airflow from the pump 110 to the suction portion 230 of the tube 210. The tube connector 205 is attached at a proximal end of the connecting portion 225 and removably secures the connecting portion 225 to the pump 110. The channel of the tube 210 extends down the length of the connecting portion 225. At a distal end of the connecting portion 225, the tube 210 branches out to form the suction portion 230.

In the embodiment of FIG. 2, the connecting portion 225 and the suction portion 230 are integrally formed of the same piece of material (i.e., have a unitary construction). To create the suction portion 230 of the tube 210, the tube's 210 single piece of material is at least partially physically split in half, thereby creating two branches 235a, 235b of the suction portion 230 and exposing the channel of the tube 210 on a medial side of each branch 235. Exposing the channel of the tube 210 connects the airflow between the pump 110 and the uterus, allowing the tube 210 to transmit the change in pressure provided by the pump 110 to the uterus. In addition, the exposed channels are beneficially located along a medial side of each branch 235 of the suction portion 230 such that the exposed channels are oriented away from an interior wall of the uterus when the insertable device 105 is inserted. This configuration prevents uterine tissue or other tissue from obstructing the exposed channels and preventing airflow when the pump 110 is actuated. In some embodiments, the orientation of the exposed channels on the suction portion 230 may vary. For example, the exposed channels may be oriented at an off-axis angle from the medial surface of the suction portion 230. In other words, the exposed channels may be oriented at an angle relative to an axis (e.g., a bisecting axis) of the medial surface. In some embodiments, the exposed channels may be located on a surface other than the medial surface of the suction portion 230 (e.g., a lateral surface of the suction portion 230). In these embodiments, channels may not be exposed after the tube 210 is split to create the two branches 235a, 235b. In other embodiments, the exposed channels on the suction portion 230 may be some combination thereof. In addition, some exposed channels may not be configured to pass biological material from the uterus. In some embodiments, the connecting portion 225 and the suction portion 230 may be separate components/pieces of material that are coupled to each other.

The bridge 215 spans between the branches 235 of the suction portion 230. Each end of the bridge 215 is attached to a distal end of a branch 235 of the suction portion 230. The bridge 215 may be attached via an interference fit (e.g., friction fit or press fit), an adhesive, a threaded interface, or some combination thereof. In the embodiment of FIG. 2, the length of the bridge 215 is sufficient enough to maintain a separation between the branches 235 of the suction portion 230. In some implementations, the manner in which the branches 235 are constructed, for example as described with respect to FIG. 3 below, the branches 235 have a natural tendency to come together in a resting state (i.e., when no external force is exerted on the branches 235). However, this tendency may cause the exposed channels on each branch 235 to become obstructed in the resting state. Thus, the bridge 215 exerts a force on each branch 235 to separate the branches 235 into a split state. This configuration prevents the branches 235 of the suction portion 230 from collapsing into each other when the pump 110 is actuated and thereby obstructing the airflow between the pump 110 and the uterus.

In addition, the bridge 215 maintains the alignment of the branches 235 of the suction portion 230 such that the exposed channels along the medial side of the suction portion 230 remain facing inward towards each other. In one embodiment this is accomplished by forming the bridge 215, which has a substantially curved body with rounded edges, directionally-limiting so that the insertable device 105 is positioned comfortably within the uterus when inserted and to prevent damage to the uterine wall, while also maintaining its orientation when inserted so as to keep the exposed channel oriented inward as discussed. In some embodiments, the shape of the bridge 215 may vary in terms of the length, width, curvature, thickness, etc. As a result, the configuration of the distal portion 120 may vary, for example, to form a circular, elliptical, triangular, or horn-shaped loop, or any other suitable geometries for placement within the uterus. Alternate embodiments of the bridge 215 will be discussed with regards to FIG. 7E. In some embodiments, the insertable device 105 may not include a bridge 215.

The seal 220 creates a seal at the opening of the uterus. In the embodiment of FIG. 2, the seal 220 is a disk positioned at a distal end of the connecting portion 225, adjacent to the suction portion 230, however in alternate embodiments it may be placed at varying locations along the connecting portion 225 depending on the size/length of the other elements. The disk may be circular, elliptical, or any other suitable geometry for sealing an opening to the uterus. The disk may or may not include a lip around its perimeter, wherein the lip may help position the seal against the uterine wall. In addition, the disk may have a convex or a concave profile. The seal 220 may be composed of semi-flexible plastics, such as silicone, polyethylene, polypropylene, or any other suitable medical-grade material. The flexible material of the seal 220 allows the seal 220 to conform to the anatomy of the uterus such that the seal 220 may be positioned against an opening of the uterus to form a seal between the uterus and an environment external to the uterus. Sealing the uterus allows the insertable device 105 to create a vacuum and maintain a negative pressure within the uterus to facilitate contraction of the uterus. In some embodiments, the seal 220 may be configured to form a seal at any point from the vulva, the cervix, the vaginal canal, or within the uterus. Additional embodiments of the seal 220 include a plurality of disks, a cup, a balloon, and a sleeve, which may be interchangeable with other components of the insertable device 105, for example as described with respect to any of the exemplary embodiments herein. These additional embodiments will each be discussed in further detail with regards to FIGS. 7A-7E.

In some embodiments, the insertable device 105 may include a sheath (not shown) that facilitates insertion of the insertable device 105 into the uterus and may additionally prevent a premature connection of the airflow from the pump 110 to the uterus. The sheath may cover a portion of the tube 210, the bridge 215, and/or the seal 220, or some combination thereof. As an example, the sheath may be in the form of a translatable outer tube that encloses a portion of the tube 210, a removable membrane that encloses distal portions of the insertable device 105, or other structures having a similar configuration. The sheath may be removed once the suction portion 230 is positioned within the uterus. Removal of the sheath may simultaneously release or position the seal 220 in the uterus to create the seal. When use of the system 100 is complete, the sheath may be re-installed onto the insertable device 105. The re-installation process may simultaneously break the seal from the seal 200 and cut off the connection of the airflow between the pump 110 and the uterus.

Figure 3:
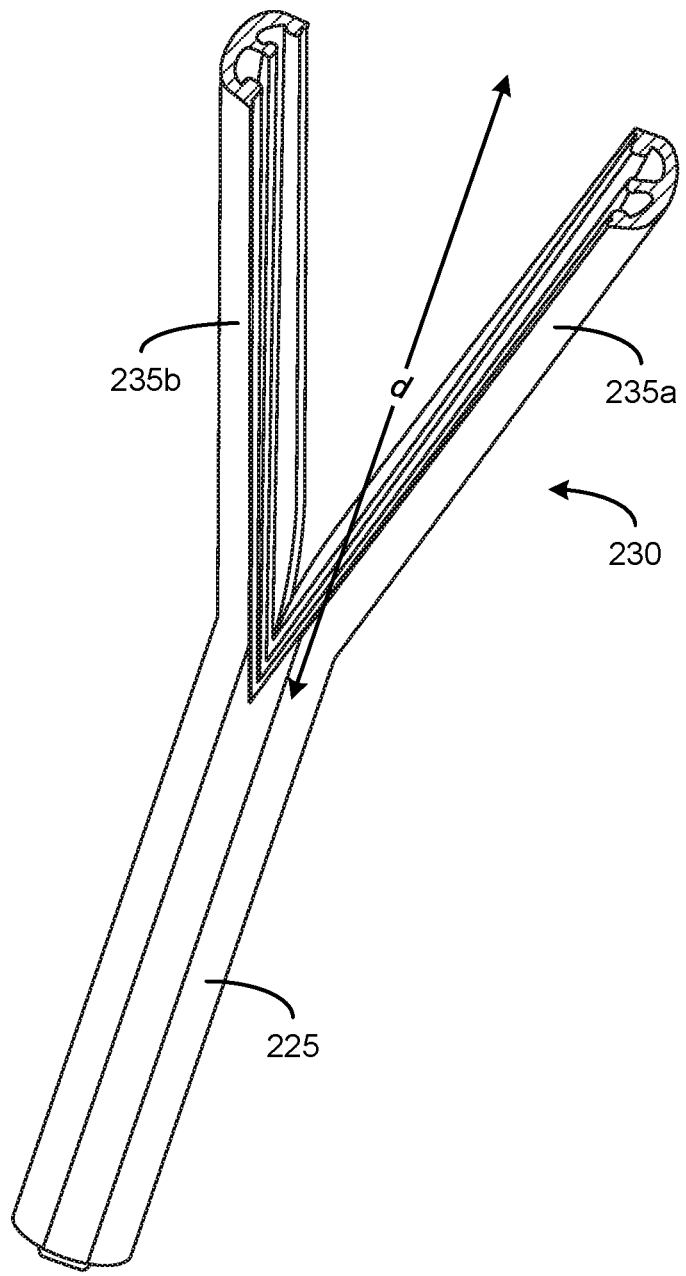
FIG. 3 illustrates a tube of the insertable device of FIG. 2, according to an embodiment.

FIG. 3 illustrates the tube 210 of the insertable device of FIG. 2, according to an embodiment. In the embodiment of FIGS. 2-3, the tube 210 is manufactured through an extrusion process, though in other embodiments the tube 210 may be manufactured in other ways. An extrusion process is used to create objects having a desired cross-sectional profile by pushing a material through a die of the desired cross-section. Materials such as silicone, polyethylene, polypropylene, or any other suitable medical-grade material may be used for the extrusion process of the tube 210. Once the extrusion is created, the extrusion may be cut to a desired length. In the embodiment of FIG. 3, the tube 210 is extruded using a semi-flexible material, which allows the insertable device to conform to the anatomy of a uterus when inserted.

In the embodiment of FIGS. 2-3, the extrusion undergoes post-processing to form the final product, the tube 210. As described with regards to FIG. 2, the tube 210 includes the connecting portion 225 and the suction portion 230. To create the suction portion 230 of the tube 210, a portion of the extrusion is at least partially split in half along its length. As illustrated in FIG. 3, the extrusion is cut from a distal end of the tube 210 down to the length of the extrusion by a distance d. The distance d is a suitable length that allows the suction portion 230 to be inserted comfortably into a uterus. In some embodiments, the die may be designed such that the extrusion includes a groove on an internal or external surface that extends down a certain length of the extrusion. The groove may facilitate the cutting process by indicating the location of the cut and acting as a guide for the tool performing the cut. In some embodiments, the groove indicates a location at which the wall thickness of the extrusion is thinner than the remainder of the extrusion. A thinner wall thickness may ease the cutting process or allow two halves of the extrusion to be separated manually to form the suction portion 230.

In some embodiments, the tube 210 is manufactured through a GeoTrans® extrusion process. In this process, the die may be designed such that the desired cross-section of the extrusion changes along the length of the extrusion. Specifically, a desired cross-section for the connecting portion 225 may differ from a desired cross-section for the suction portion 230. For example, the cross-section of the connecting portion 225 may be substantially cylindrical or elliptical while the cross-section of the suction portion 230 may include one or more channels. In some embodiments, the cross-section of the extrusion may change along its length in an alternating pattern. The change in cross-section between the connecting portion 225 and the suction portion 230 may be designed to occur transitionally or abruptly.

In addition, the die may be designed such that the cross-section of the tube 210 includes surface features on an internal surface of the tube 210. Example surface features are illustrated in FIG. 3, wherein each branch 235 of the suction portion 230 includes a middle protrusion that extends down the length of the internal surface of the tube 210. The surface features may aid the flow of air and biological materials within the tube 210, which will be discussed in further detail with regards to FIGS. 4-5. By manufacturing the tube 210 through an extrusion process, minimal post-processing is required to form the final product of the insertable device 105. Moreover, once a die is manufactured for a desired extrusion, large quantities of the extrusion may be produced at a fast rate (e.g., thousands per day), especially if the die is configured to create multiple extrusions simultaneously. This production may significantly reduce overall manufacturing costs, as well as reduce overall device complexity by reducing the number of components in the finished device. In addition, the design of the insertable device 105, specifically the split state of the branches 235 and the bridge 215 that maintains separation of the branches 235, provides greater design flexibility for the surface features on the channel as the branches 235 are not required to bend or curve substantially.

Figure 4A:
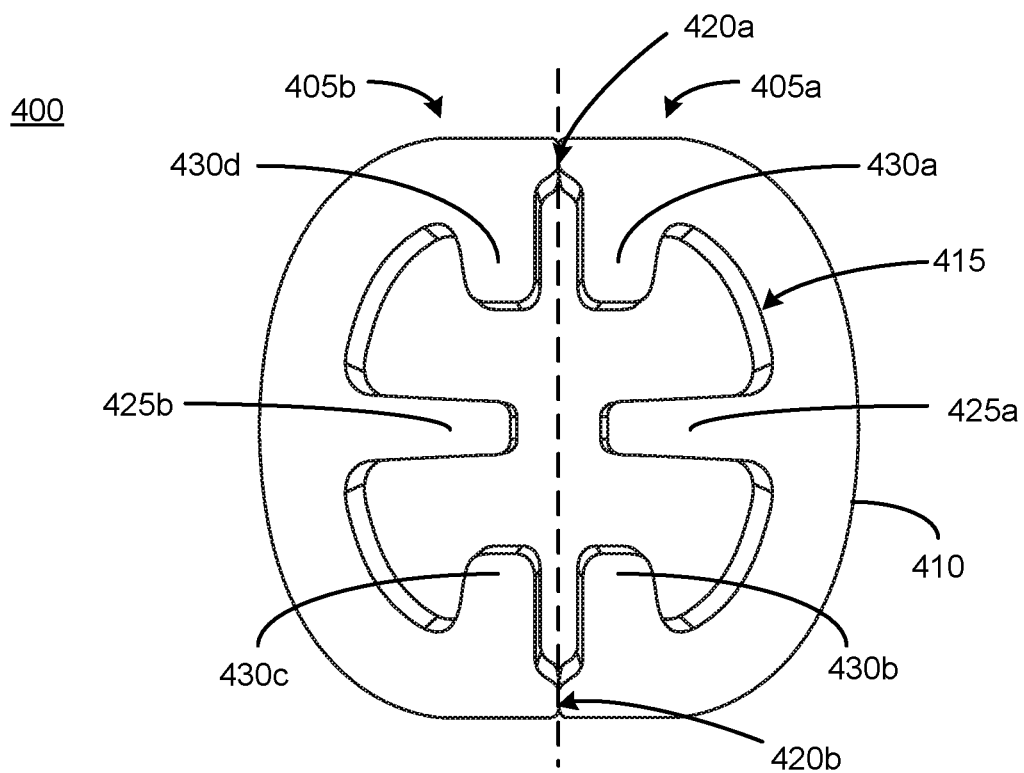
FIGS. 4A and 4B illustrate cross-sectional views of an extrusion for creating the tube of FIG. 3, according to an embodiment.

FIG. 4A illustrates a cross-sectional view of an extrusion 400 for creating the tube 210, according to an embodiment. Specifically, a cross-section of the suction portion 230 of the tube 210 is shown before two halves 405a, 405b of the extrusion 400 are split to create the separate branches of the suction portion 230. In the embodiment of FIG. 4A, the extrusion 400 includes an outer wall 410 and a channel 415. The outer wall 410 forms the external boundary of the tube 210. The outer wall 410 surrounds the channel 415, through which air and biological materials can pass. As illustrated in FIG. 4A, the outer wall 410 is substantially of uniform thickness. The thickness of the outer wall 410 may be between approximately 1 to 2.5 millimeters (mm). The outer wall 410 includes two grooves 420a, 420b that are located on opposite edges of the outer wall. In the embodiment of FIG. 4A, the grooves 420a, 420b are located on an internal and external surface of the outer wall 410, such that the thickness of the outer wall 410 narrows at the grooves 420a, 420b. As described with regards to FIG. 3, the grooves 420a, 420b facilitate the separation of the two halves 405a, 405b to form the separate branches of the suction portion 230 of the tube 210. In the embodiment of FIG. 4A, the grooves 420a, 420b extend down the length of the tube 210 for the suction portion 230. In some embodiments, the connecting portion 225 may not include the grooves 420a, 420b and only the suction portion 230 includes the grooves 420a, 420b. This configuration may prevent propagating the separation of the two halves 405a, 405b into the connecting portion 225. For embodiments in which the grooves 420a, 420b extend down the length of the tube 210 for the connecting portion 225, the cross-sectional view shown in FIG. 4A also illustrates the cross-section of the connecting portion 225.

In the embodiment of FIG. 4A, the surface of the channel 415 includes the following surface features: protrusions 425a, 425b and protrusions 430a, 430b, 430c, 430d. As illustrated in FIG. 4A, the surface features are arranged such that the cross-section of the extrusion 400 is substantially symmetrical. This configuration ensures that each branch of the suction portion 230 includes the same surface features once the extrusion 400 is split along the grooves 420a, 420b. The protrusions 425a, 425b are positioned at a middle portion of the channel 415 and protrude into the center of the channel 415 towards each other. The protrusions 430a, 430b, are positioned to the right of grooves 420a, 420b, respectively, and protrude towards each other, while protrusions 430c, 430d, are positioned to the left of grooves 420b, 420a, respectively, and protrude towards each other. This configuration of protrusions 425, 430 divides the channel 415 into smaller channels, which provides each branch of the suction portion 230 with certain properties, discussed in further detail with regards to FIG. 4B.

Figure 4B:
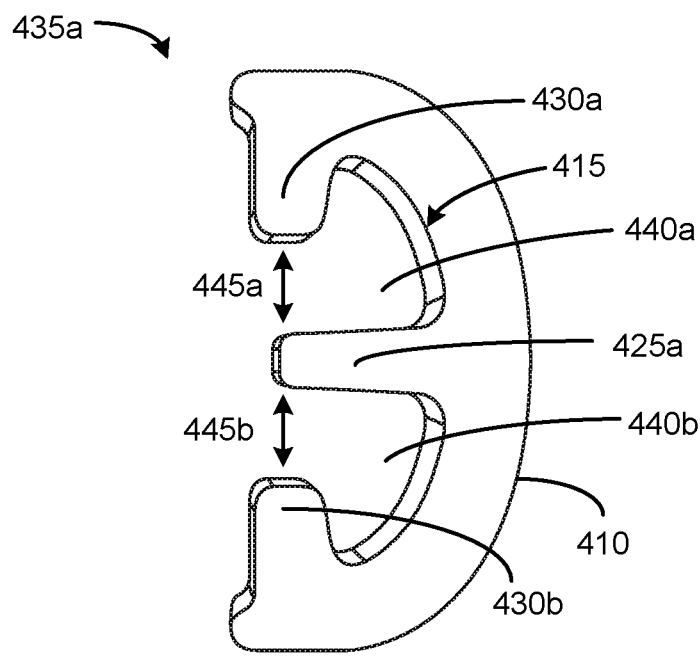

FIG. 4B illustrates a cross-sectional view of a branch 435a of the suction portion 230, according to an embodiment. Specifically, the cross-section shown is of the half 405a after the two halves 405a, 405b of the extrusion 400 are split to create separate branches of the suction portion 230. The half 405a forms the branch 435a. While branch 435b is not shown, it is formed by the half 405b. As illustrated in FIG. 4B, the protrusions 425a, 430a, 430b divide the channel 415 into two smaller channels 440a, 440b, wherein each channel has a respective opening 445a, 445b. As described with regards to FIG. 2, openings in the suction portion 230 allow fluid communication between the uterus and the pump 110. Dividing the channel 415 into smaller channels 440a, 440b distributes the airflow from the pump 110 and increases the number of pathways by which air and biological materials can travel. Thus, if a single pathway becomes obstructed by biological materials, other pathways remain accessible, and the system 100 can effectively maintain a negative pressure inside the uterus. In addition, to further prevent the channels 445a, 445b from becoming obstructed, the openings 445a, 445b are located on a medial side of the respective branches 435 such that when the suction portion 230 is inserted into the uterus, the outer wall 410 faces the uterine wall and the openings 445a, 445b. This configuration prevents uterine tissue or other tissue from obstructing the openings 445a, 445b and preventing airflow when the pump 110 is actuated.

In the embodiment of FIG. 4B, the openings 445a, 445b are configured to allow biological materials of a certain size through the openings 445a, 445b and into the channels 440a, 440b such that these biological materials may be removed from the uterus and collected in the collection container 115. In the embodiment of FIG. 4B, the size of each opening 445a, 445b is between approximately 1 to 4 millimeters (mm). In some embodiments, the size of each opening 445a, 445b is between 2 to 3.5 millimeters (mm). Openings of this size may additionally be configured to break up masses of biological material that have formed a clot. By breaking up the masses, the openings 445a, 445b are able to prevent obstruction of the airflow from the pump 110 and allow the biological material to be collected in the collection container 115.

Figure 5A:
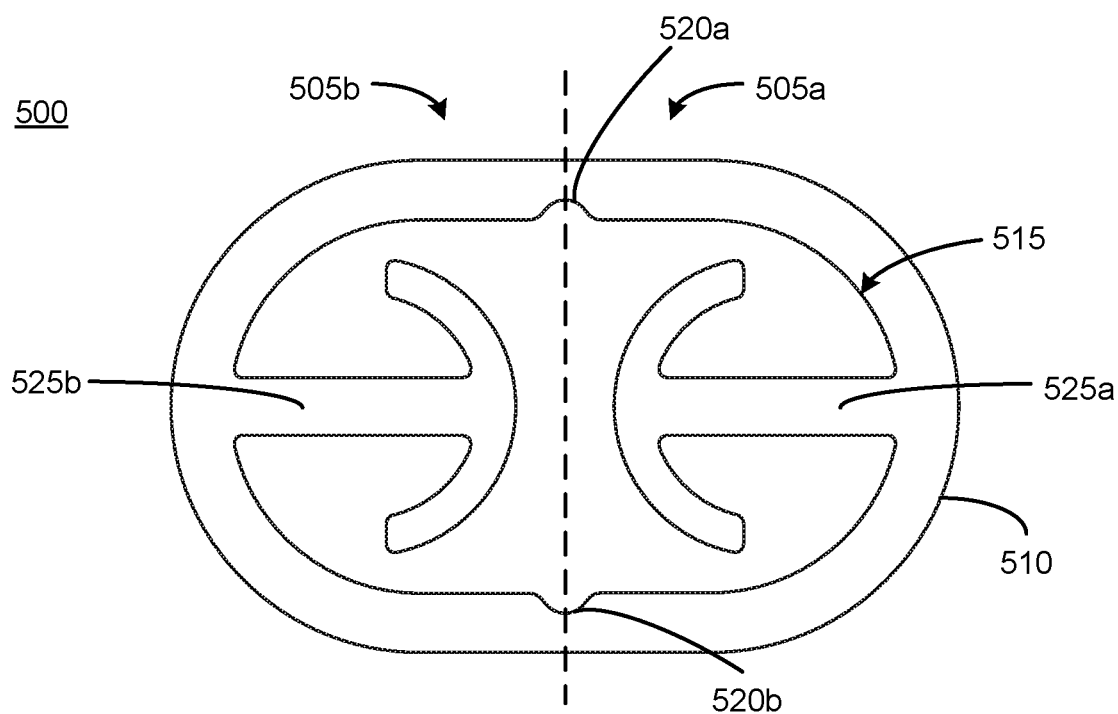
FIGS. 5A and 5B illustrate cross-sectional views of an additional embodiment of an extrusion for creating the tube of FIG. 3.

FIG. 5A illustrates a cross-sectional view of an additional embodiment of an extrusion 500 for creating the tube 210. Specifically, a cross-section of the suction portion 230 of the tube 210 is shown before two halves 505a, 505b of the extrusion 500 are split to create the separate branches of the suction portion 230. Similar to extrusion 400, the extrusion 500 includes an outer wall 510 and a channel 515. The outer wall 510 forms the external boundary of the tube 210. The outer wall 510 surrounds the channel 515, through which air and biological materials can pass. As illustrated in FIG. 5A, the outer wall 510 is substantially of uniform thickness. The thickness of the outer wall 510 may be between approximately 1 to 2.5 millimeters (mm). The outer wall 510 includes two grooves 520a, 520b that are located on opposite edges of the outer wall. Similar to grooves 420a, 420b, the grooves 520a, 520b facilitate the separation of the two halves 505a, 505b to form the separate branches of the suction portion 230 of the tube 210. In the embodiment of FIG. 5A, the grooves 520a, 520b are located only on an internal surface of the outer wall 510, but, in some embodiments, the grooves 520a, 520b may be located on both an internal and external surface of the outer wall 510.

Figure 5B:
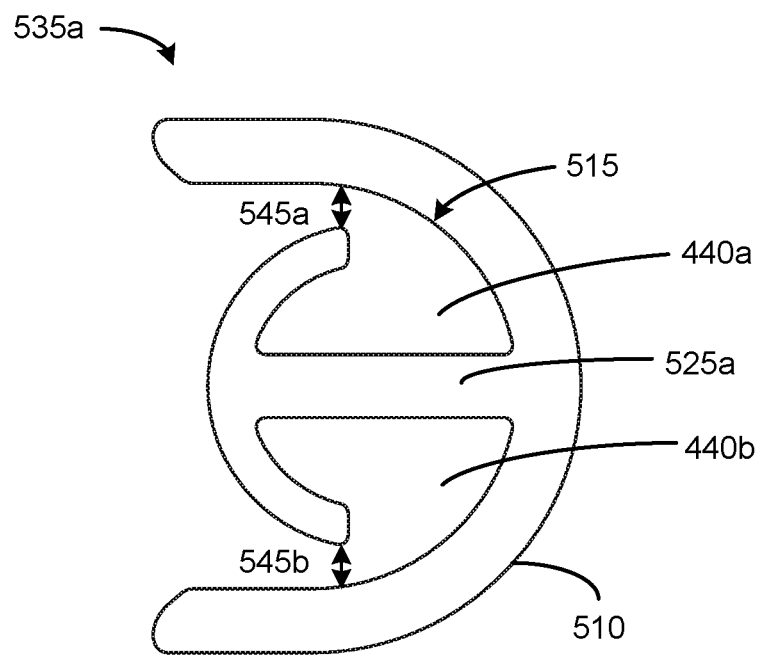

In the embodiment of FIG. 5A, the surface of the channel 515 includes the following surface features: protrusions 525a, 525b. As illustrated in FIG. 5A, the protrusions 525a, 525b are arranged such that the cross-section of the extrusion 500 is substantially symmetrical. This configuration ensures that each branch of the suction portion 230 includes the same surface features once the extrusion 500 is split along the grooves 520a, 520b. The protrusions 525a, 525b are positioned at a middle portion of the channel 515 and protrude into the center of the channel 515 towards each other. In the embodiment of FIG. 5A, each protrusion 525a, 525b has a distal end that extends in a different direction to the portion of the protrusion that extends from the outer wall. In the illustrated embodiment, this different direction of extension forms a shape similar to an umbrella, wherein each protrusion 525 includes a middle support structure with a curved arm extending from each side of the support structure. In other embodiments, other shapes may be formed, such as T-shaped protrusions, and so on. Regardless of the exact shape, this general configuration of protrusions 525a, 525b divides the channel 515 into smaller channels, which provides each branch of the suction portion 230 with certain properties, discussed in further detail with regards to FIG. 5B FIG. 5B illustrates a cross-sectional view of a branch 535a of the suction portion 230. Specifically, the cross-section shown is of the half 505a after the two halves 505a, 505b of the extrusion 500 are split to create separate branches of the suction portion 230. The half 505a forms the branch 535a. While branch 535b is not shown, it is formed by the half 505b. As illustrated in FIG. 5B, the protrusion 525a divides the channel 515 into two smaller channels 540a, 540b wherein each channel has a respective opening 545a, 545b. Similar to the embodiment of FIG. 4, dividing the channel 515 into smaller channels 540a, 540b distributes the airflow from the pump 110 and increases the number of pathways by which air and biological materials can travel. In the embodiment of FIG. 5B, the openings 545a, 545b are distanced apart from each other due to the configuration of the protrusion 525a. Separating the openings 545a, 545b by a distance may decrease the likelihood of the openings 545a, 545b becoming obstructed by biological materials at the same time, potentially by the same mass of biological material. Thus, if a first opening becomes obstructed by biological materials, at least a second opening remains accessible, and the system 100 can effectively maintain a negative pressure inside the uterus. In addition, to further prevent the channels openings 545a, 545b from becoming obstructed, the openings 545a, 545b are located on a medial side of the respective branches 535 such that when the suction portion 230 is inserted into the uterus, the outer wall 510 faces the uterine wall and the openings 545a, 545b. This configuration prevents uterine tissue or other tissue from obstructing the openings 545a, 545b and preventing airflow when the pump 110 is actuated.

Similar to the embodiment of FIG. 4B, in the embodiment of FIG. 5B, the openings 545a, 545b are configured to allow biological materials of a certain size through the openings 545a, 545b and into the channels 540a, 540b such that these biological materials may be removed from the uterus and, in some embodiments, collected in the collection container 115. In the embodiment of FIG. 4B, the size of each opening 545a, 545b is between approximately 1 to 4 millimeters (mm). Openings of this size may additionally be configured to break up a mass of biological material (e.g., a clot or clump of tissue). By breaking up the mass, the openings 545a, 545b are able to prevent obstruction of the airflow from the pump 110 and allow the biological material to be collected in the collection container 115.

Figure 6A:
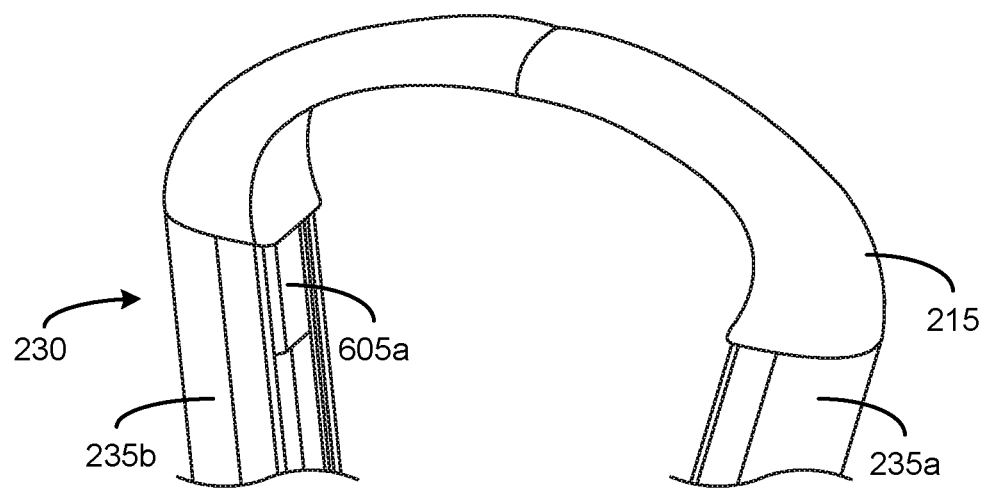
FIGS. 6A and 6B illustrate a method for attaching a bridge to a tube of FIG. 5, according to an embodiment.

FIG. 6A illustrates a method for attaching the bridge 215 to the tube 210, according to an embodiment. As illustrated in FIG. 6A, a first end of the bridge 215 is attached to a distal end of branch 235a of the suction portion 230, and a second end of the bridge 215 is attached to a distal end of branch 235b of the suction portion 230. This configuration of the suction portion of the tube 210 ensures that the branches 235 are separated and remain in a split state when inserted into the uterus.

In the embodiment of FIG. 6A, each end of the bridge 215 includes a mating protrusion 605a (605b not shown) that extends from an end of the bridge 215. To secure the bridge 215 to the suction portion 230, the mating protrusions 605a, 605b are inserted into a channel of the branches 235b, 235a, respectively. The mating protrusions 605a, 605b may be inserted with an interference fit (e.g., friction fit or press fit), an adhesive, a threaded interface, or some combination thereof. In the embodiment of FIG. 6A, the mating protrusions 605a, 605b are silicone bonded to the respective branches 235b, 235a.

Figure 6B:
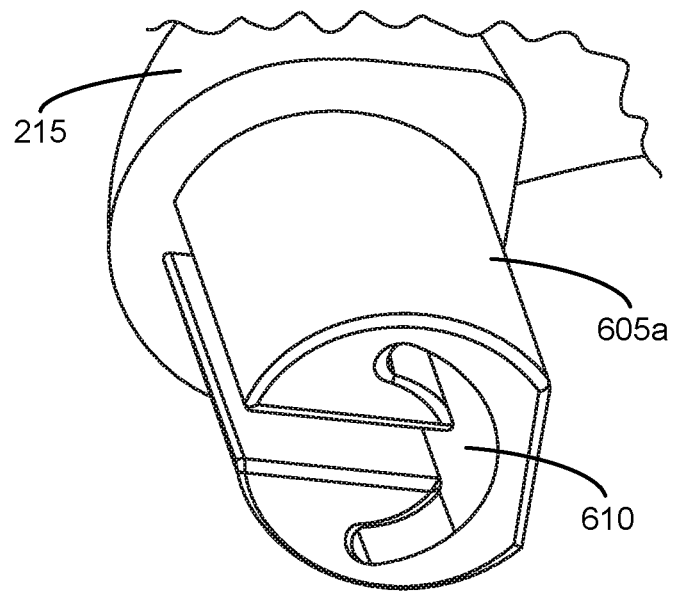

FIG. 6B illustrates mating protrusion 605a that secures a first end of the bridge 215 to the branch 235a, according to an embodiment. The mating protrusion 605a may include a cavity 610 that complements surface features located on a channel of the branch 235a. In the embodiment of FIG. 6B, the shape of the cavity 610 is designed to complement the shape of the surface features described with regards to FIG. 5B. In this configuration, the surface feature 525a may be inserted into the cavity 610, which may improve the stability and security of the attachment between the bridge 215 and the branch 235a. In addition, the cavity 610 provides a greater surface area for silicone bonding the mating protrusions 605a, 605b to the respective branches 235b, 235a. Other embodiments may have a cavity 610 designed to complement the shape of the surface features illustrated in FIGS. 4A and 4B or any other channel surface feature configuration.

In some embodiments, the bridge 215 may be configured to transmit the airflow from the tube 210. The bridge 215 may include channels or holes along a medial side of the bridge 215, and the mounting protrusions 605a, 605b may include channels that couple the airflow of the suction portion 230 to the bridge 215. This configuration provides additional pathways by which the airflow and/or biological materials can travel.

FIGS. 7A-7E illustrate additional embodiments of an insertable device. As described with regards to FIG. 2, an insertable device includes several components, such as a tube connector, a tube having a connecting portion and a suction portion, a bridge, and a seal. Each component may have a variety of designs, which will be discussed in further detail. In addition, different designs of the components may be interchangeable and combined in several ways to create different configurations of an insertable device.

Figure 7A:
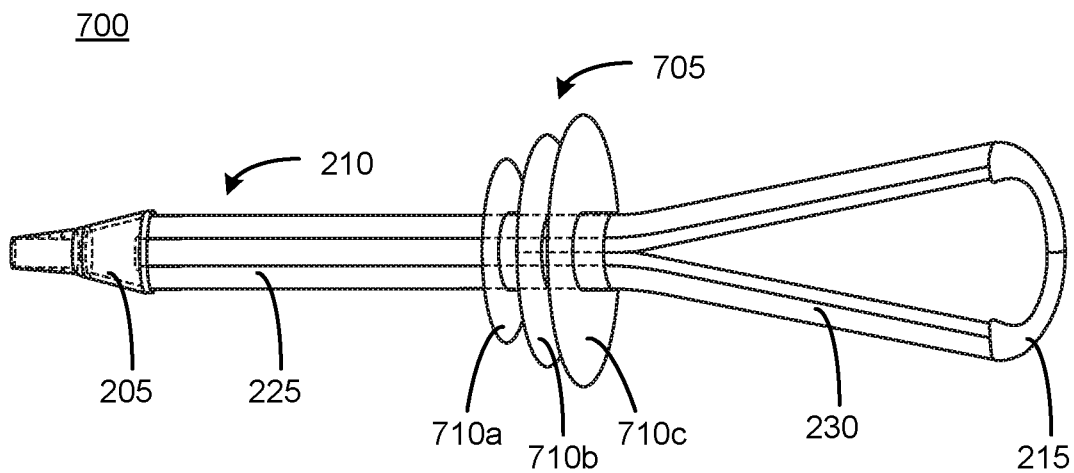
FIGS. 7A-7E illustrate additional embodiments of an insertable device.

FIG. 7A illustrates an insertable device 700, according to an embodiment. In the embodiment of FIG. 7A, the insertable device 700 includes the tube connector 205, the tube 210 having the connecting portion 225 and the suction portion 230, the bridge 215, and a seal 705. Similar to the embodiment of the seal discussed with regards to FIG. 2, the seal 705 creates a seal at the opening of the uterus. The seal 705 is composed of three disks 710a, 710b, 710c positioned at a distal end of the connecting portion 225, adjacent to the suction portion 230. Each disk 710 may be composed of a semi-flexible material, such as silicone, polyethylene, polypropylene, or any other suitable medical-grade material, allowing each disk 710 to conform to the anatomy of the uterus. The diameter of each disk 710 incrementally decreases such that the largest disk 710c is closest to the suction portion 230 and the smallest disk 710a is farthest away from the suction portion 230. In this configuration, the decreasing diameters of the disks 710 may improve the ability of the seal 705 to be positioned against an opening of the uterus such that each disk 710 may abut the uterine wall to form a seal between the uterus and an environment external to the uterus. Having a seal including three disks 710 may improve the quality of the seal formed and provide redundancy in maintaining the seal. Other embodiments may include a varying number of disks that may be positioned at different distances relative to each other (e.g., two disks that are spaced farther apart or ten disks that are spaced closer together).

Figure 7B:
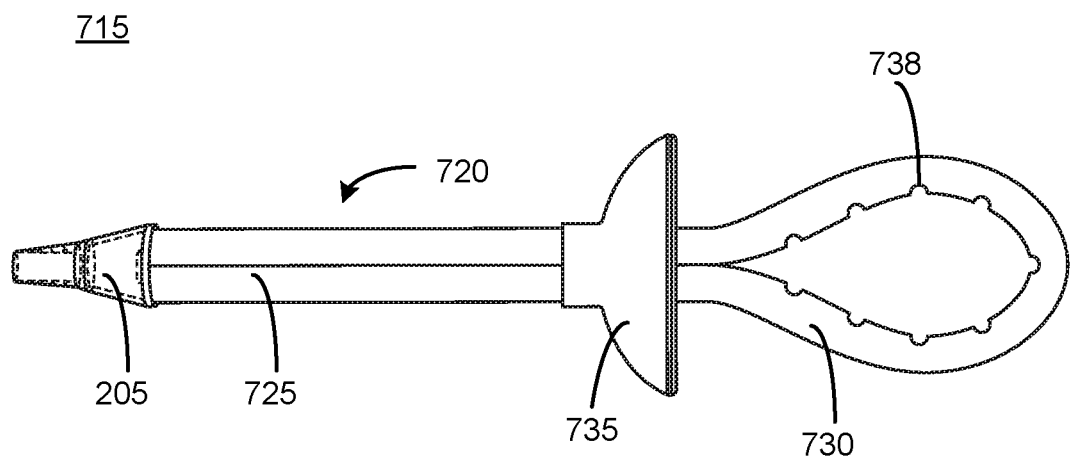

FIG. 7B illustrates an insertable device 715, according to an embodiment. In the embodiment of FIG. 7B, the insertable device 700 includes the tube connector 205, a tube 720 having a connecting portion 725 and a suction portion 730, and a seal 735. Similar to the embodiment of the tube discussed with regards to FIG. 2, the tube 720 acts as a conduit for air and biological materials. The tube 720 may comprise one or more channels that couple airflow from the pump 110 to the uterus to transmit a change in pressure inside the uterus. In the embodiment of FIG. 7B, the tube 720 is a flexible tube that is folded to form the connecting portion 725 and the suction portion 730. The sections of the tube 720 forming the connecting portion 725 may be adjoined via an adhesive, one or more over-molded components secured around the tube 720, or a heat shrink wrap placed over the tube 720. Meanwhile, the suction portion 730 remains a loop. In this configuration, the construction of the tube 720 ensures that the alignment of the openings and/or channels on the medial side of the loop of the suction portion 730 remain facing away from the uterine wall upon insertion. In addition, this configuration eliminates the need for a connecting element (e.g., bridge 215) between branches of the tube, which may decrease the cost of manufacturing the tube 720. However, the rigidity of the tube 720 needs to be appropriately determined such that the tube 720 may be flexible enough to form the loop of the suction portion 730 yet rigid enough to prevent the suction portion 730 from potentially deforming and obstructing the openings and/or channels on the medial side of the loop. In addition, the design of the surface features on a surface of the channel of the tube 720 may be limited due to the desired curvature of the tube 720.

In the embodiment of FIG. 7B, the suction portion 730 includes one or more openings 738 located along a medial side of the loop such that the openings 738 are oriented away from an interior wall of the uterus when the insertable device 105 is inserted. This configuration prevents uterine tissue or other tissue from obstructing the openings 738 and preventing airflow when the pump 110 is actuated. The openings 738 may be circular, elliptical, polygonal, or any other suitable shape that allows air and biological materials to travel through. In some embodiments, the openings 738 may be channels that extend along the medial side of the loop.

The seal 735 creates a seal at an opening of the uterus. The seal 735 is positioned at a distal end of the connecting portion 225, adjacent to the suction portion 730. In the embodiment of FIG. 7B, the seal 735 is shaped similar to a cup, wherein a bottom portion of the cup shape is configured to abut the uterine wall at an opening of the uterus upon insert of the insertable device 730 into the uterus. The seal 735 is composed of a semi-flexible material, such as silicone, polyethylene, polypropylene, or any other suitable medical-grade material, that allow the seal 735 to conform to the anatomy of the uterine wall.

Figure 7C:
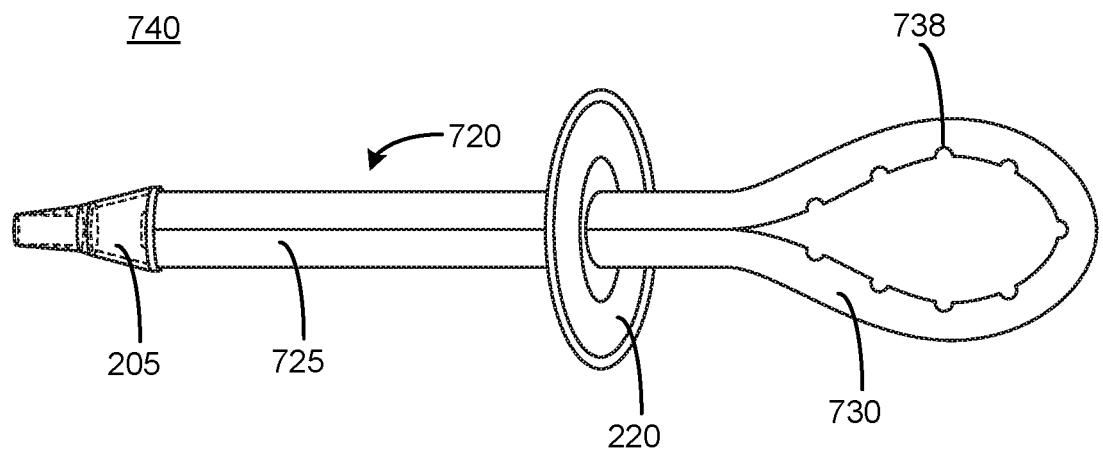

FIG. 7C illustrates an insertable device 740, according to an embodiment. In the embodiment of FIG. 7C, the insertable device 740 includes the tube connector 205, the tube 720 having the connecting portion 725 and the suction portion 730, and the seal 220. The insertable device 740 combines the tube configuration described with regards to FIG. 7B with the seal configuration described with regards to FIG. 2.

Figure 7D:
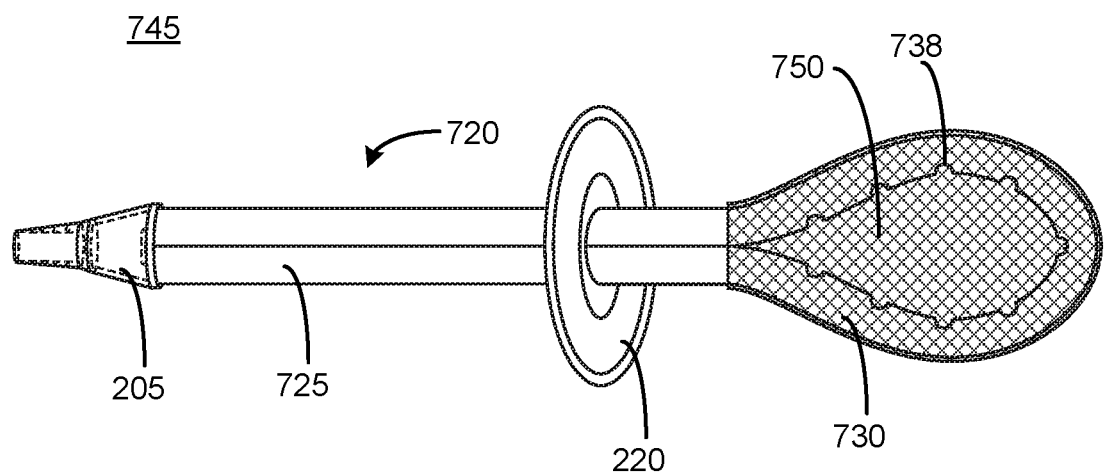

FIG. 7D illustrates an insertable device 745, according to an embodiment. The insertable device 745 is an embodiment of insertable device 740. In the embodiment of FIG. 7D, the insertable device 745 includes the tube connector 205, the tube 720 having the connecting portion 725 and the suction portion 730, the seal 220, and a shield 750. The shield 750 is a porous mesh that allows particles of a certain size to pass through the mesh. In the embodiment of FIG. 7D, the shield 750 encloses the suction portion 730 to prevent uterine tissue from obstructing the openings 738 while allowing other biological materials (e.g., blood) to pass through. The shield 750 may be composed of gauze, nylon, or other suitable materials that may be placed within the uterus.

Figure 7E:
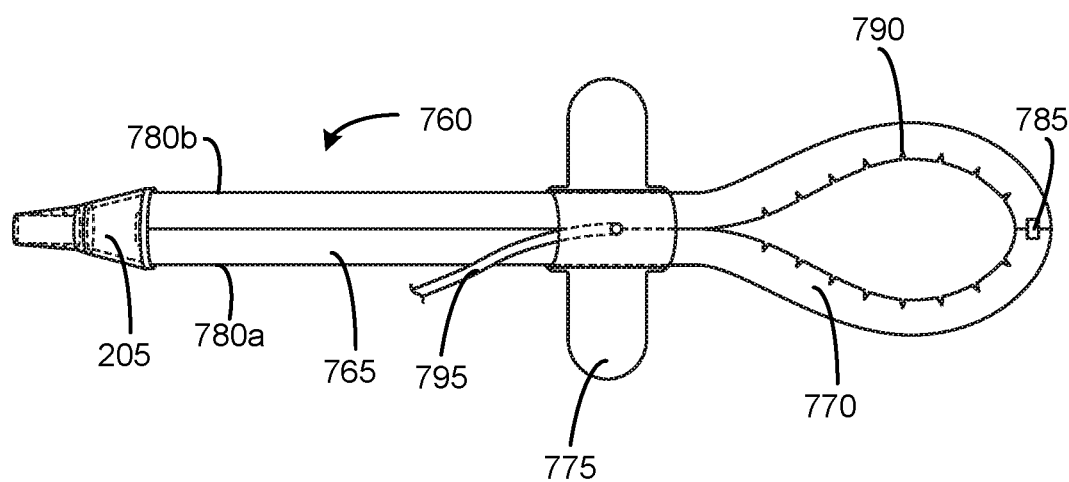

FIG. 7E illustrates an insertable device 755, according to an embodiment. In the embodiment of FIG. 7E, the insertable device 755 includes the tube connector 205, a tube 760 having a connecting portion 765 and a suction portion 770, and a seal 775.

The tube 760 acts as a conduit for air and biological materials. While the tube 760 is similar in geometry to tube 720, the tube 760 is made of two individual tubes 780a, 780b rather than a single folded tube. Each tube 780a, 780b includes an internal channel extending down the length of the tube. In the embodiment of FIG. 7E, tubes 780a, 780b are positioned adjacent to each other such that a portion of the tubes 780a, 780b can be adjoined to form the connecting portion 765. The tubes may be adjoined via an adhesive, one or more over-molded components secured around the connecting portion 765, or a heat shrink wrap placed over the tube connecting portion 765. The remaining portions of the tubes 780a, 780b are curved to mate an end of tube 780a to an end of tube 780b, forming a loop to create the suction portion 770. The ends of the tubes 780a, 780b may be coupled together using a plug 785. In the embodiment of FIG. 7E, a first end of the plug 785 is inserted into a channel of tube 780a, and a second end of the plug 785 is inserted into a channel of tube 780b. The plug 785 may be secured within the tubes 780a, 780b using an adhesive. The plug 785 may include openings or channels to form a continuous pathway for airflow and/or biological materials through the tube 760. In some embodiments, the plug 785 may be designed to fit over the ends of the tubes 780a, 780b as a cross tube connector. For embodiments in which the suction portion of the tube comprises two separate branches that are to be connected, the connecting element (such as bridge 215 or plug 785) can have a variety of configurations and be of any size, depending upon the rigidity of the tube and given that the connecting element appropriately mates the branches such that the openings or channels on each branch remain unobstructed and allow a vacuum to be created within the uterus upon insertion of the insertable device.

In the embodiment of FIG. 7E, the suction portion 770 includes one or more openings 790. The openings 790 are created by skiving the external surface of the suction portion 770. A skiving process carves out notches in the surface of the suction portion 770. The openings 790 are located along a medial side of the loop such that the openings 790 are oriented away from an interior wall of the uterus when the insertable device 105 is inserted. This configuration prevents uterine tissue or other tissue from obstructing the openings 790 and preventing airflow when the pump 110 is actuated.

The seal 775 creates a seal at an opening of the uterus. In the embodiment of FIG. 7E, the seal 775 is a sleeve or a balloon that can be inflated once the suction portion 770 is positioned within the uterus. The seal 775 may be inserted while flattened, allowing the seal 775 to be properly positioned before the seal 775 is inflated. The seal 775 may be positioned within the vaginal canal, cervix, or uterus. In the embodiment of FIG. 7E, the seal 775 includes a tube 795 that may connect to the pump 110 to inflate the seal 775. The seal 775 may be composed of silicone, polyethylene, polypropylene, or any other suitable medical-grade material.

Figure 8:
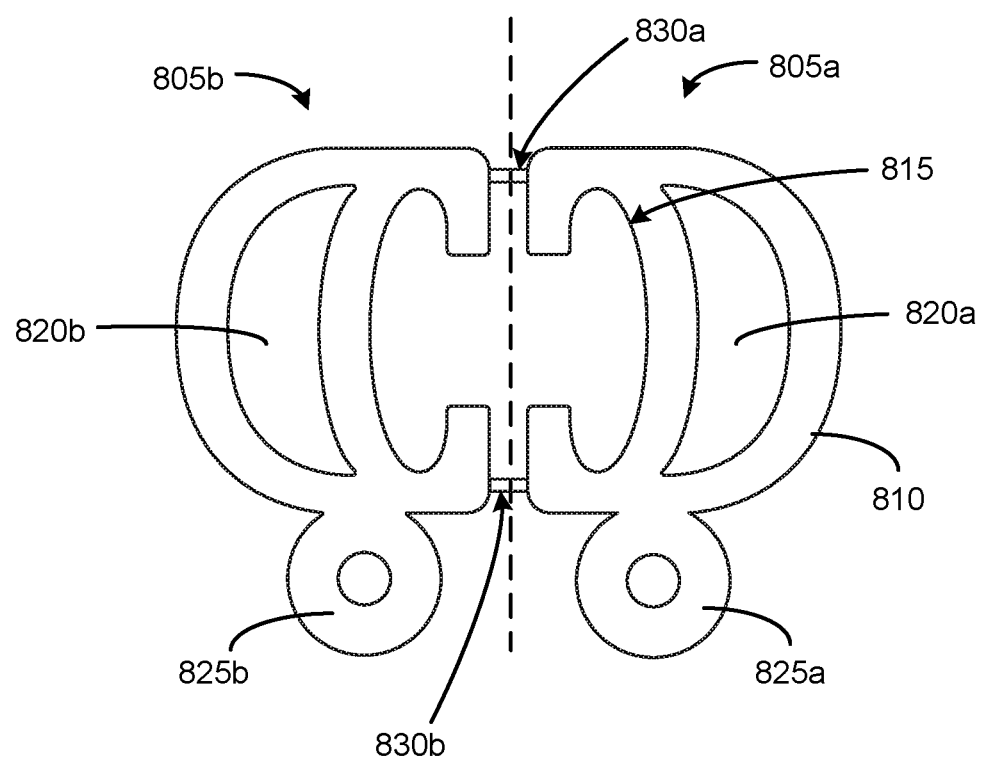
FIG. 8 illustrates a cross-sectional view of an additional embodiment of an extrusion for creating a tube of FIG. 3.

FIG. 8 illustrates a cross-sectional view of an additional embodiment of an extrusion 800 for creating the tube 210. Specifically, a cross-section of the suction portion 230 of the tube 210 is shown before two halves 805a, 805b of the extrusion 800 are split to create the separate branches of the suction portion 230. In the embodiment of FIG. 8, the extrusion 800 includes an outer wall 810, channel 815, channels 820a, 820b, and rings 825a, 825b. The outer wall 810 forms the external boundary of the tube 210. The outer wall 810 encloses the channels 815, 820a, 820b. As illustrated in FIG. 8, the outer wall 810 is substantially of uniform thickness. The thickness of the outer wall 810 may be between approximately 1 to 2.5 millimeters (mm). The outer wall 810 includes two grooves 830a, 830b that are located on opposite edges of the outer wall 810. In the embodiment of FIG. 8, the grooves 830a, 830b are located on an internal and external surface of the outer wall 810, such that the thickness of the outer wall 810 narrows at the grooves 830a, 830b. As described with regards to FIG. 3, the grooves 830a, 830b facilitate the separation of the two halves 805a, 805b to form the separate branches of the suction portion 770 of the tube 760. In the embodiment of FIG. 8, once the two halves 805a, 805b are separate to form the branches of the suction portion 770, the branches are curved towards each other to form a loop, wherein a first end of a first branch mates with a first end of a second branch. To secure the ends of the branches together, a pin may be inserted into the rings 825a, 825b. The pin may be adhered within the rings 825a, 825b.

Once the two halves 805a, 805b are separated, the channel 815 is exposed to allow fluid communication between the pump 110 to the uterus. The wall between the channel 815 and the respective channels 820a, 820b may include one or more openings (e.g., holes or channels) such that biological material may enter the channel 815 and flow through to the channels 820a, 820b. In this configuration, the channels 820a, 820b act as drain channels. This configuration may help the channel 815 remain unobstructed.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

What is claimed:
1. An insertable device comprising:
   a tube having a connecting portion configured for coupling to a vacuum source, and a suction portion configured for insertion into a uterus, the suction portion including a single loop having a first branch and a second branch that are separated from each other, the first branch and the second branch respectively including an outer wall and a channel having a surface protrusion; and a bridge fluidically coupled to the suction portion, the bridge having a mating protrusion extending from distal ends thereof to secure the bridge to the suction portion via insertion into the channel of the first branch and the second branch, each mating protrusion having a cavity that complements and receives via insertion the surface protrusion of the first branch and the second branch; and a plurality of disk-shaped seals positioned along a length of the connecting portion proximal to the suction portion, the diameter of each disk-shaped seal incrementally decreases such that a largest disk-shaped seal of the plurality of disk-shaped seals is closest to the suction portion and the smallest disk-shaped seal of the plurality of disk-shaped seals is farthest away from the suction portion.

2. The insertable device of claim 1, wherein the connecting portion and the suction portion are separate components that couple together.

3. The insertable device of claim 1, wherein the connecting portion and the suction portion have a unitary construction.

4. The insertable device of claim 1, wherein the tube is manufactured as an extrusion.

5. The insertable device of claim 4, wherein the extrusion comprises a constant cross-section.

6. The insertable device of claim 4, wherein the extrusion comprises at least one groove extending down the length of the suction portion of the extrusion.

7. The insertable device of claim 6, wherein the at least one groove is positioned between edges of the extrusion.

8. The insertable device of claim 1, wherein the bridge separates the distal ends of the first branch and the second branch by a distance.

9. The insertable device of claim 8, wherein the length of the bridge prevents the first branch and the second branch from collapsing into each other.

10. The insertable device of claim 1, wherein the tube is composed of a flexible material.

11. The insertable device of claim 1, wherein the connecting portion is configured to couple to a container that collects biological materials from the uterus.

12. The insertable device of claim 11, wherein the container is configured to indicate an amount of biological materials collected.

13. An insertable device comprising:
a tube having a connecting portion for insertion into a uterus, the tube formed as a single loop having a first branch and a second branch that are separated from each other, the first branch and the second branch respectively including an outer wall and a channel having a surface protrusion;

a bridge fluidically coupled to the tube, the bridge having a mating protrusion extending from distal ends thereof to secure the bridge to the tube via insertion into the channel of the first branch and the second branch, each mating protrusion having a cavity that complements and receives via insertion the surface protrusion of the first branch and the second branch; and a plurality of disk-shaped seals positioned along a length of the tube, the diameter of each disk-shaped seal incrementally decreasing in size.

14. The insertable device of claim 13, wherein the tube is manufactured as an extrusion.

15. The insertable device of claim 14, wherein the extrusion comprises a constant cross-section.

16. The insertable device of claim 14, wherein the extrusion comprises at least one groove extending down the length of a portion of the extrusion.

17. The insertable device of claim 16, wherein the at least one groove is positioned between edges of the extrusion.

18. The insertable device of claim 13, wherein the bridge separates the distal ends of the first branch and the second branch by a distance.

19. The insertable device of claim 18, wherein the length of the bridge prevents the first branch and the second branch from collapsing into each other.

20. The insertable device of claim 13, wherein the tube is composed of a flexible material.

* * * * *